United States Patent [19]

Pelosi, Jr.

[11] 4,066,672
[45] Jan. 3, 1978

[54] DIETHYL[5-(4-NITROPHENYL)FURFURYL]-AMINE HYDROCHLORIDE

[75] Inventor: Stanford S. Pelosi, Jr., Norwich, N.Y.

[73] Assignee: Morton-Norwich Products, Inc., Norwich, N.Y.

[21] Appl. No.: 780,857

[22] Filed: Mar. 24, 1977

[51] Int. Cl.² ............................................ C07D 307/52
[52] U.S. Cl. ................................. 260/347.7; 424/285
[58] Field of Search ..................................... 260/347.7

[56] References Cited

U.S. PATENT DOCUMENTS

| 2,185,220 | 1/1940 | Nabenhauer | 260/347.7 X |
| 3,096,348 | 7/1963 | Denss et al. | 260/347.7 |

OTHER PUBLICATIONS

Dunlop, The Furans, ACS Monograph Series, (1953), pp. 242 to 246.

*Primary Examiner*—Richard L. Raymond
*Attorney, Agent, or Firm*—Anthony J. Franze

[57] ABSTRACT

Diethyl[5-(4-nitrophenyl)furfuryl]amine hydrochloride is useful as an anti-inflammatory agent.

1 Claim, No Drawings

DIETHYL[5-(4-NITROPHENYL)FURFURYL]AMINE HYDROCHLORIDE

This invention relates to the compound diethyl[5-(4-nitrophenyl)furfuryl]amine hydrochloride and a method for its preparation.

This compound possesses pharmacologic activity. It is particularly useful as an anti-inflammatory agent as evidenced by its ability to inhibit edema induced in rats by the administration of carrageenin. Thus, when administered at a dose of 300 mg/kg suspended in a vehicle such as aqueous methyl cellulose per os to rats receiving carrageenin, edema associated with that substance is inhibited by 69% [Winter et al., P.S.E.B.M. 111:544 (1962)].

The compound of this invention is readily prepared. Currently, it is preferred to react 5(4-nitrophenyl)furfuryl chloride with diethylamine in the presence of a solvent such as benzene.

In order that this invention may be fully available to and understood by those skilled in the art, the method now preferred for making it is described:

A solution of 47 g (0.20 mole) of 5-(4-nitrophenyl)furfuryl chloride and 58 g (0.80 mole) of diethylamine in 250 ml of benzene was heated under reflux for 8 hrs. After cooling to room temperature, the solid diethylamine hydrochloride (28 g, 95%) was collected by filtration and discarded. The filtrate was washed with 10% aqueous $Na_2CO_3$ and water and dried over $MgSO_4$. The solvent was removed on a rotary evaporator, and the residual oil was dissolved in 250 ml of anhydrous ether and 50 ml of absolute methanol. The solution was treated with hydrogen chloride, and the solid which was deposited was collected by filtration to give 45 g (73%) of diethyl[5-(4-nitrophenyl)furfuryl]amine hydrochloride. Recrystallization from $CH_3NO_2$ gave an analytical sample, m.p. 220°–237° (dec.).

Anal. Calcd. for $C_{15}H_{18}N_2O_3 \cdot HCl$: C, 57.97; H, 6.16; N, 9.02.

Found: C, 57.74; H, 6.22; N, 9.17.

What is claimed is:

1. The compound diethyl[5-(4-nitrophenyl)furfuryl]amine hydrochloride.

* * * * *